(12) United States Patent
Tietze

(10) Patent No.: US 11,325,888 B2
(45) Date of Patent: May 10, 2022

(54) METHOD FOR THE SYNTHESIS OF MONOPROTECTED BIFUNCTIONAL PRODRUGS AND ANTIBODY DRUG CONJUGATES BASED THEREON AS WELL AS A METHOD FOR PREPARING ANTIBODY DRUG CONJUGATES

(71) Applicant: GEORG-AUGUST-UNIVERSITÄT GÖTTINGEN STIFTUNG ÖFFENTLICHEN RECHTS, Göttingen (DE)

(72) Inventor: Lutz F. Tietze, Göttingen (DE)

(73) Assignee: Georg-August-Universitaet Goettingen Stiftung Oeffentlichen Rechts, Goettingen (DE)

( * ) Notice: Subject to any disclaimer, the term of this patent is extended or adjusted under 35 U.S.C. 154(b) by 0 days.

(21) Appl. No.: 16/638,289

(22) PCT Filed: Aug. 10, 2018

(86) PCT No.: PCT/EP2018/071718
§ 371 (c)(1),
(2) Date: Feb. 11, 2020

(87) PCT Pub. No.: WO2019/030367
PCT Pub. Date: Feb. 14, 2019

(65) Prior Publication Data
US 2020/0172484 A1 Jun. 4, 2020

(30) Foreign Application Priority Data
Aug. 11, 2017 (EP) .................................... 17185977

(51) Int. Cl.
| *C07D 209/60* | (2006.01) |
| *A61K 45/06* | (2006.01) |
| *A61K 47/68* | (2017.01) |
| *C07H 17/02* | (2006.01) |

(52) U.S. Cl.
CPC ........ *C07D 209/60* (2013.01); *A61K 47/6803* (2017.08); *C07H 17/02* (2013.01); *A61K 45/06* (2013.01)

(58) Field of Classification Search
CPC .. C07D 209/60; A61K 45/06; A61K 47/6803; C07H 17/02
USPC ........................................... 514/411; 548/427
See application file for complete search history.

(56) References Cited

FOREIGN PATENT DOCUMENTS

| WO | 2009/017394 A1 | 2/2009 |
| WO | 2015/023355 A1 | 2/2015 |
| WO | 2016/040723 A1 | 3/2016 |
| WO | 2017/072295 A1 | 5/2017 |

OTHER PUBLICATIONS

Tietze et al: "Photoactivatable Prodrugs of Highly Potent Duocarmycin Analogues for a Selective Cancer Therapy", Chemistry—A European Journal, vol. 19, No. 5, pp. 1726-1731, Dec. 7, 2012.

*Primary Examiner* — Joseph R Kosack
*Assistant Examiner* — Sagar Patel
(74) *Attorney, Agent, or Firm* — WCF IP

(57) ABSTRACT

The present invention relates to a method for the synthesis of compounds useful in the preparation of antibody drug conjugates (ADC), namely, monoprotected dimeric bifunctional prodrugs based on duocarmycin analogs. In a further aspect, compounds obtained by the method according to the present invention are provided. The monoprotected bifunctional prodrug is used for preparing antibody drug conjugates composed of an antibody moiety and the monoprotected bifunctional prodrug. The antibody compound conjugates thus obtained are provided. Further, a method of preparing an antibody drug conjugate composed of two identical or two different antibody moieties is provided as well as the antibody compound conjugate containing two different antibody moieties accordingly. These conjugates can be used in pharmaceutical compositions, in particular, for use in treatment of tumors, e.g. for use in ADC therapy.

8 Claims, 1 Drawing Sheet

METHOD FOR THE SYNTHESIS OF MONOPROTECTED BIFUNCTIONAL PRODRUGS AND ANTIBODY DRUG CONJUGATES BASED THEREON AS WELL AS A METHOD FOR PREPARING ANTIBODY DRUG CONJUGATES

The present invention relates to a method for the synthesis of compounds useful in the preparation of antibody drug conjugates (ADC), namely, monoprotected dimeric bifunctional prodrugs based on duocarmycin analogs. In a further aspect, compounds obtained by the method according to the present invention are provided. The monoprotected bifunctional prodrug is used for preparing antibody drug conjugates composed of an antibody moiety and the monoprotected bifunctional prodrug. The antibody compound conjugates thus obtained are provided. Further, a method of preparing an antibody drug conjugate composed of two identical or two different antibody moieties is provided as well as the antibody compound conjugate containing two different antibody moieties accordingly. These conjugates can be used in pharmaceutical compositions, in particular, for use in treatment of tumors, e.g. for use in ADC therapy.

PRIOR ART

The various forms of cancer disease require individual therapy concepts. In response to the complexity of a tumor disease, most of today's clinically applied treatment methods represent combinations of different therapeutic approaches. The surgical removal may be the method of choice in case of surgically accessible and clearly defined tumors. However, if the tumor is more difficult to access or affects vital structures, radiation treatment is the method of choice as well as treatment by chemotherapy. In a more advanced stage, in which metastases have already developed or at least the risk of metastasation exists, chemotherapy is usually performed immediately. In addition, methods of hormone therapy, immunotherapy and therapy with angiogenesis inhibitors and kinase inhibitors are used in tumor therapy.

Actually, chemotherapy is currently the most important treatment method in case of metastases or in case of systemic tumors although it is often associated with severe side effects such as disorder of the blood picture, immune deficiency, mucositis, fever, nausea, vomiting. That is, most of the chemotherapeutic agents are distributed throughout the body via the blood circulation so that they can reach all cells. However, chemotherapeutic agents act on the human cells systemically in general, that is they prevent cell proliferation or they act cytotoxic that is they may cause the death of cells. Typically, chemotherapeutic agents do not distinguish between cancer cells and normal cells. The difference is that tumor cells are rapid proliferating cell types while normal cells are slow proliferating cells. However, since the fast-growing non-tumor cells of the treated person are also affected, in particular, those of the bone marrow, the hair roots and the intestinal epithelia cells, severe side effects occur. One example of cytotoxic agents used in chemotherapy includes alkylating agents. The alkylating agents are a numerically significant structurally very diverse class of extremely reactive substances. In some cases after a prior activation of the medicament or prodrug into a carbocation, the active compound reacts as electrophile, in particular, with the nucleic acids, forming covalent bonds. Thus, cross-linking of the DNA, abnormal base pairings or strand breaks occur preventing replication and eventually lead to cell death. Typical examples of alkylating drugs are cyclophosphamide but also cisplatin. A group of particularly effective alkylating agents include the natural antibiotic CC1065, a cyclopropylpyrroloindole (CPI) derivate, the duocarmycins and cyclopropylbenzoindole (CBI) derivatives, the yatekemycin as well as derivatives and analogs of this class of natural prodrugs. Due to the necessity of chemotherapeutic treatments, the strong side effects of a large part of clinically used drugs and the occurrences of resistance to many known chemotherapeutic agents, a continuous development in the field of chemotherapeutic agents is necessary.

To reduce the side effects in chemotherapy, new concepts have been developed that exploit the genotypic and phenotypic properties of tumor cells and enable a targeted activation of reversible prodrugs directly at the side of action. Such targeted activation is found in the so called ADEPT concept (antibody directed enzyme prodrug therapy). In this case, antibody enzyme congregates are used, which directly converts the tumor to a transformation of the non-toxic prodrug into the drug and achieves a higher selectivity. This binary therapy approach consists of two steps. First, a certain amount of an antibody enzyme conjugate is applied which is then distributed throughout the organism by blood circulation.

The conjugate binds to specific antigens on tumor cell surfaces or is degraded or excreted by the body. If the unbound antibody enzyme congregate can no longer be detected, the application of the prodrug takes place in the second step. The typically non-toxic prodrug is also distributed throughout the entire organism and is selectively toxicated in the tumor tissue by virtue of the enzyme which is usually only present on the tumor surface in the form of the antibody enzyme congregate. The released drug then unfolds its toxic effect after penetration through the cell membrane, while the enzyme remains active on the outer side of the tumor cell and can activate further prodrug molecules. A cleavage of the prodrugs by body specific enzyme system should not occur as far as possible in the course of this approach, since otherwise the activity of the therapy would be reduced or abolished. These advantages of previously known prodrugs have, however, a too small difference in cytotoxicity between the prodrug and the drug generated therefrom (QIC50) as well as too low cytotoxicity (IC50) for the drug formed itself.

As a guideline: The QIC50 values of the prodrug in the presence of the enzyme should be greater than 1000 and the cytotoxicity of the underlying drug should have an IC50 value of less than 10 nM.

Clinical studies have already been carried out for the ADEPT concept. It has been shown that the ADEPT concept is suitable for selective tumor therapy but there is still a need for improvement on various points in order to enable selective and efficient therapy.

Another approach in the context of targeted treatment of malignant tumors is the prodrug monotherapy. There, the presence of enzymes overexpressed in tumors which are able to cleave a corresponding prodrug with release of the corresponding drug is desired. An example of this possible enzyme is the β-D-glucuronidase which could be detected in increased concentrations in necrotic areas of tumor tissue. Alternatively, conjugates of drugs and tumor-specific ligands can also be used for selective targeting in cancer therapy. One of the issues where improvement is desired, is the provision of new and effective prodrugs that have a high cytotoxicity difference between the prodrug and the corresponding drug, a high cytotoxicity of the drug and a short plasma median time in the drug. In addition, there is a need for new types of bifunctional prodrugs on the basis of duocarmycin analoga for the ADC therapy (antibody drug conjugate).

The ADC is an important class of highly potent biopharmaceutical drugs designed as a target therapy for the treatment of subjects suffering e.g. from cancer. In ADCs, the antibodies are linked to the biological active principle also called payload or prodrug/drug. The drug may be in form of a prodrug converted to the active principle in the targeted cell or may be present as a drug effective after binding to the target.

With ADC the targeting capabilities of monoclonal antibodies are combined with the cytotoxic activity of active agents or preforms of said active agents. Due to the specificity of the monoclonal antibodies, directed targeting to the cancer cells is possible. Thus, more effective treatment of cancer cells is possible while having less severe side effects, namely, on healthy cells.

Although already some ADC products are marketed, it is expected to have a great potential for ADC pharmaceuticals. Cleavable and non-cleavable linkers exist for attaching the antibody moiety to the anti-cancer agent or active principle or precursor thereof. However, the linkage may affect the toxicity of the active principle.

Various embodiments have been described in the art for linking the antibody moiety or other binding partners to the payload, in particular to CBI components.

For example, WO 2009/017394 describes substituted CC-1065 analogs and their conjugates. Other bifunctional compounds are described e.g. in DE 10 2015 118 490 identifying new bifunctional prodrugs and drugs based on CC-1065 analogs.

Tietze, L. F. et al., Chem. Eur. J. 2013, 19, 1726-1731 describe photoactivatable prodrugs of highly potent duocarmycin analogues for a selective cancer therapy. Therein, a scheme of photochemical activation of dimeric seco-drugs is provided. The theoretical reaction scheme is given showing an intermediate theoretical compound 16 of a monoprotected bifunctional prodrug. Of note, shown is the theoretical reaction of the bifunctional prodrug to the seco-drug via the theoretical intermediate of a mono-seco-drug. The mono-seco-drug shown in the scheme is of theoretic nature only since the reaction will be directly from the bifunctional prodrug to the seco drug when applying irradiation. Hence, the compound 16, the mono-seco-drug, was not isolated or characterized. A selective cleavage of only one protecting group of the bifunctional product is not possible as shown in this scheme, but the reaction directly produce the seco-drug which immediately reacts further to the drug 18 as shown in scheme 4.

However, the bifunctional compounds described in the art are linked to binding entities, like antibodies symmetrically, that is, on both CBI subunits of the bifunctional compound. However, it is desirable to provide bifunctional prodrugs having different functional groups at both conjugation sides of the two subunits.

BRIEF DESCRIPTION OF THE PRESENT INVENTION

The aim of the present invention is to provide new bifunctional prodrugs based on duocarmycin analogs for ADC therapy which allow heterogeneous derivatization suitable for ADC therapy.

The present invention describes the synthesis of said analogs for ADC therapy accordingly. It has been recognized that a conjugation of the antibody at one subunit of the bifunctional prodrug is possible, thus, achieving linkage to at least one of the two OH groups while the other OH group being essential for the required Winstein cyclization necessary for the conversion of the prodrug into the active drug is available for other purposes. Thus, it is possible to provide a bifunctional prodrug comprising the necessary moiety allowing later Winstein cyclization while at the second OH group of the second subunit, the antibody or any binding moiety is linked to the bifunctional prodrug. Further, one may envisage to provide heterogeneous bifunctional prodrugs being differently conjugated with functional groups, thus, enabling the Winstein cyclization of the two CBI subunits at different time points.

The compounds according to the present invention do not require the introduction of any additional functional group on the payload or drug for the attachment of e.g. the antibody. Contrary to the teaching of DE 10 2015 118 490, binding of the binding moiety, like the antibody, is not in the linker moiety but on at least one of the two subunits of the prodrug.

The compounds described in the prior art all have the same functional group at both conjugation sides and, thus, would have the same molecular mechanisms of cleavage and cancer cell recruitment.

The present invention now allows for independent and different modification of the two OH groups of the two subunits, which cleavage are necessary for the activation and transformation of the prodrug into the active drug.

Thus, in a first aspect, a method is provided for the synthesis of a compound of general formula I

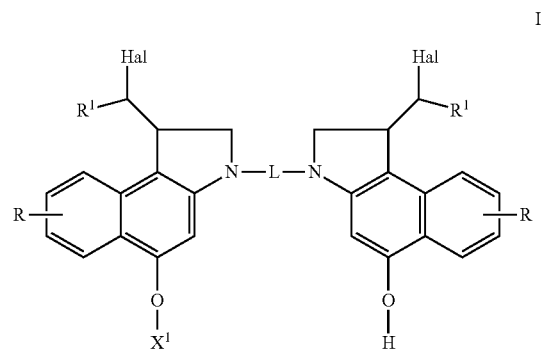

wherein Hal is F, Cl, Br, or I;
R is H or an optionally substituted $C_1$-$C_4$ alkyl group, an optionally substituted $C_1$-$C_4$ alkoxy group, an optionally substituted aryl group, an optionally substituted heteroaryl group, an optionally substituted $C_1$-$C_4$ alkyl carboxy $C_1$-$C_4$ alkyl group, Hal, CN, an optionally substituted $C_1$-$C_4$ alkylsulfonyl group, an optionally substituted arylsulfonyl group, or an $NR_z$ group as defined below;
$R_1$ is H or a $C_1$-$C_4$ alkyl group or a $C_1$-$C_4$ alkoxy group;
$X_1$ is a protecting group;
L is a connecting group for covalent linkage whereby L has the general structure Z—Y—Z';
Z and Z' are independently from one another selected from C=O, OC=O,
$SO_2$, NRz, $NR_2$, C=O, C=$ONR_z$, wherein each $R_z$ is independently from one another selected from H, optionally substituted $C_1$-$C_4$ alkyl group or optionally substituted $C_1$-$C_4$ acyl;

wherein Y is an optionally substituted $C_1$-$C_{10}$ alkyl group, a group of structure (VIII)

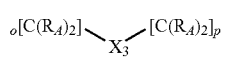

wherein o and p are independently from one another selected from an integer of 1 to 20, whereby o and p may be the same integer or a different integer, $X_3$ is i) N, S or O, or ii) an aryl group or a heteroarylgroup, wherein $[C(R_a)_2]_O$ and $[C(R_a)_2]_p$ are present in the metaposition of said aryl group or said heteroaryl group, each $R_A$ is independently from one another selected from H or an optionally substituted $C_1$-$C_4$ alkyl group or an optionally substituted $C_1$-$C_4$ acyl group; comprising the step of reacting a compound of formula II

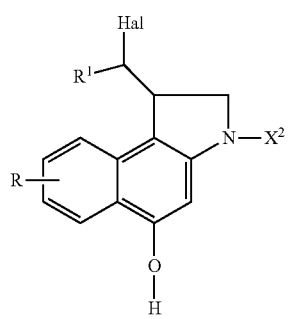

wherein R, $R_1$, and Hal are defined as above and $X_2$ is a protecting group which may be identical or different to $X_1$ above, with a deprotecting agent for deprotecting the $X_2$ group from the compound of formula II;

subsequently, reacting the deprotected compound of formula II with a compound of formula III

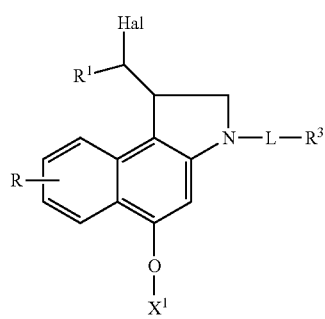

wherein the substituents Hal, $R_1$, $X_1$ and R are defined as above and L is a connecting group as defined above, $R_3$ is selected from Hal, in particular, Cl and Br, and OH in the presence of a coupling agent and a base to obtain a compound of formula I.

In a further aspect, the present invention provides compounds allowing coupling of the binding moiety, like the antibody moiety via the free OH group at one subunit of the bifunctional compound while the other OH group of the second subgroups is protected.

In another aspect, a method for preparing an ADC is described using the compound of formula I according to the present invention. In addition, said antibody compound conjugate obtainable by the method according to the present invention is provided. Moreover, a method for preparing an ADC conjugate composed of two identical or two different antibody moieties and a compound according to formula I is provided as well as said ADC obtainable by this method.

Finally, pharmaceutical compositions containing the compounds according to the present invention and the ADC according to the present invention are described as well as the use of the compounds according to the present invention or the ADC according to the present invention for treatment of tumors e.g. for use in ADEPT therapy or in ADC therapy.

BRIEF DESCRIPTION OF THE DRAWINGS

FIG. 1 shows the reactions of the method according to the present invention to arrive at a compound of general formula I.

DETAILED DESCRIPTION OF THE PRESENT INVENTION

Figure 1:
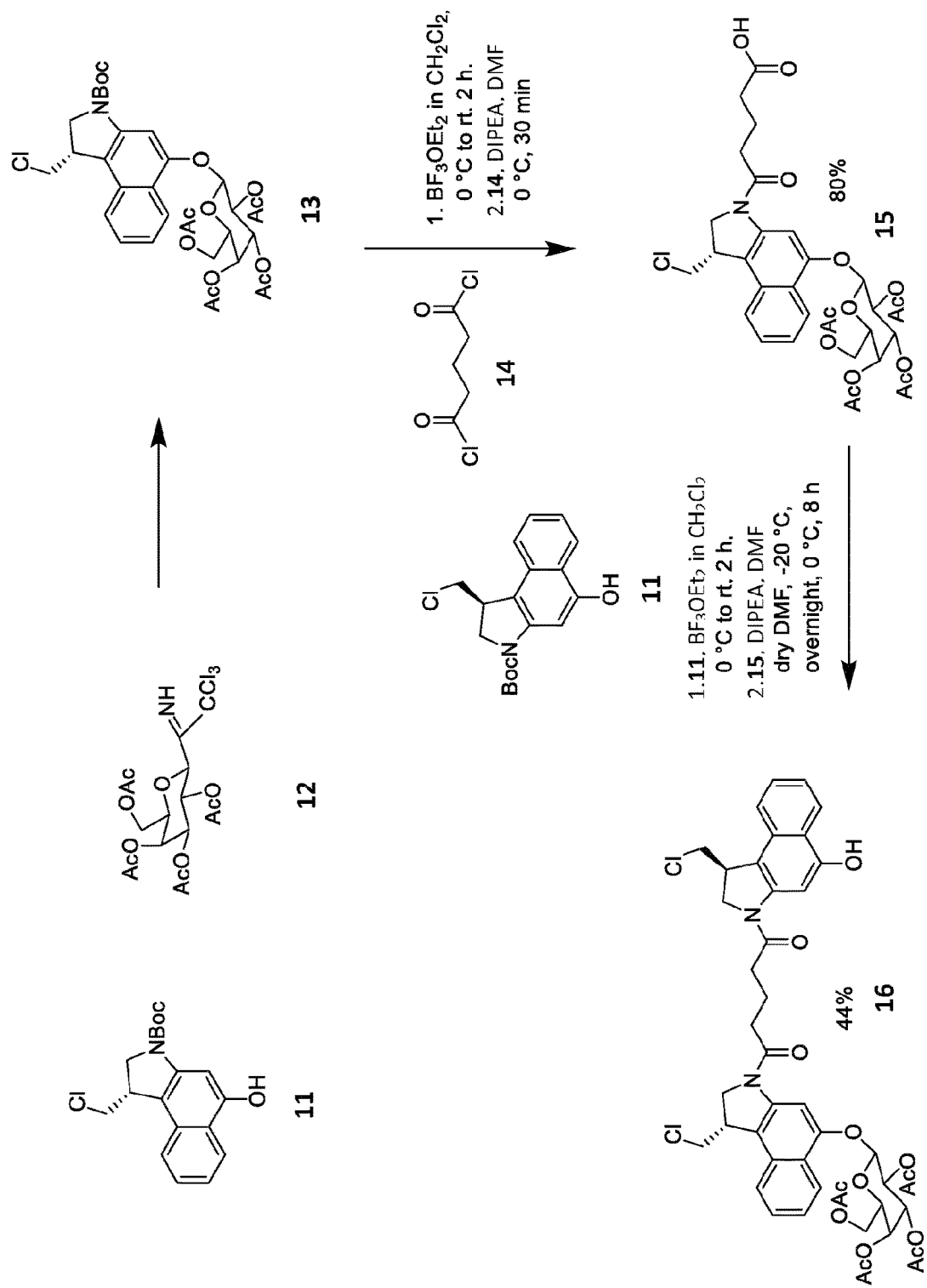
FIG. 1.

The present inventors aim in providing a method for the synthesis of new intermediates and prodrugs for compounds suitable in cancer therapy.

In a first aspect, a method is provided for the synthesis of a compound of general formula I

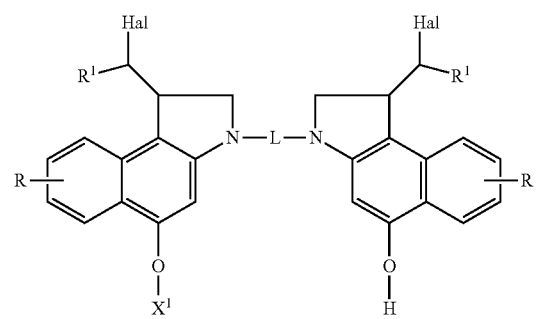

wherein Hal is F, Cl, Br, or I;

R is H or an optionally substituted $C_1$-$C_4$ alkyl group, an optionally substituted $C_1$-$C_4$ alkoxy group, an optionally substituted aryl group, an optionally substituted heteroaryl group, an optionally substituted $C_1$-$C_4$ alkyl carboxy $C_1$-$C_4$ alkyl group, Hal, CN, an optionally substituted $C_1$-$C_4$ alkylsulfonyl group, an optionally substituted arylsulfonyl group, or an $NR_z$ group as defined below;

$R_1$ is H or a $C_1$-$C_4$ alkyl group or a $C_1$-$C_4$ alkoxy group;

$X_1$ is a protecting group;

L is a connecting group for covalent linkage whereby L has the general structure Z—Y—Z';

Z and Z' are independently from one another selected from C=O, OC=O, $SO_2$, NRz, $NR_2$C=O, C=ONRz, wherein each $R_z$ is independently from one another selected from H, optionally substituted $C_1$-$C_4$ alkyl group or optionally substituted $C_1$-$C_4$ acyl;

wherein Y is an optionally substituted $C_1$-$C_{10}$ alkyl group, a group of structure (VIII)

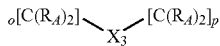

wherein o and p are independently from one another selected from an integer of 1 to 20, whereby o and p may be the same integer or a different integer, $X_3$ is i) N, S or O, or ii) an aryl group or a heteroarylgroup, wherein $[C(R_a)_2]_o$ and $[C(R_a)_2]_p$ are present in the metaposition of said aryl group or said heteroaryl group, each $R_A$ is independently from one another selected from H or an optionally substituted $C_1$-$C_4$ alkyl group or an optionally substituted $C_1$-$C_4$ acyl group; comprising the step of reacting a compound of formula II

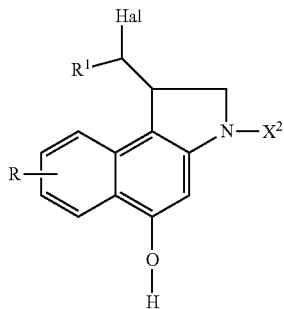

wherein R, $R_1$, and Hal are defined as above and $X_2$ is a protecting group which may be identical or different to $X_1$ above, with a deprotecting agent for deprotecting the $X_2$ group from the compound of formula II;

subsequently, reacting the deprotected compound of formula II with a compound of formula III

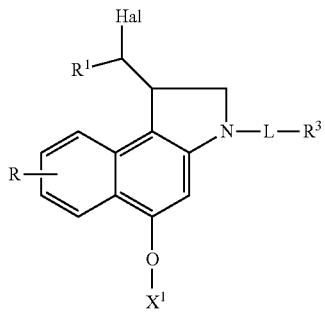

wherein the substituents Hal, $R_1$, $X_1$ and R are defined as above and L is a connecting group as defined above, $R_3$ is selected from Hal, in particular, Cl and Br, and OH in the presence of a coupling agent and a base to obtain a compound of formula I.

The present invention now allows for independent and different modification of the two OH groups at the 5' position of the benzoindol of the two subunits of bifunctional CBI based prodrugs. The cleavage of at least one of said two OH groups is required for the activation and transformation of said one subunit into an active drug.

The ADC which can be prepared using the present invention, e.g. is composed of an antibody moiety and the compound of formula I according to the present invention or a compound being deprotected either wherein $X_1$ is H or wherein the $X_1$ residue is deprotected, e.g. when $X_1$ is a tetraacetyl-beta-D-galactoside, the deprotected $X_1$ is beta-D-galactoside.

The attached antibody can be firstly cleaved off via pH-labile groups at low pH within the lysosomes and subsequently a first rearrangement to the toxic CBI unit takes place. In a second step, the rearrangement of the second toxic CBI unit can be triggered by enzymatic cleavage of the $X_1$ unit, e.g. a galactose unit based on the β-galactosidase activity in the lysosomes but also in other cell components, such as the endoplasmatic reticulum, thereby provoking cytotoxicity. A two-step activation, namely, a first toxic phase followed by a second toxic phase, could be advantageous by providing a better or longer efficacy or with few or less side effects.

The compound according to formula I allows to attach an antibody at only one phenolic OH group or at both groups. For example, if both OH groups are conjugated with an antibody, the present invention allows for conjugation of different antibodies at each side. This would have the advantage that two different tumors specifically epitopes could be used, which would further increase the specificity of the ADC therapy.

The method according to the present invention is shown in scheme 1 outlining the steps accordingly. Namely, a compound (13) according to formula IV wherein $X_1$ is a protected galactoside, namely protected by acetyl groups, $X_4$ is Boc, R is H and $R_1$ is H while Hal is Cl, is obtained by reacting compound 11 with compound 12, thus, resulting in the compound 13 of structure III with the two protecting groups $X_1$ and $X_4$. Compound 13 is reacted with compound 14 exemplifying structure VII wherein $R_5$ and $R_6$ are Cl, Z and Z' are C=O and Y is a propyl group.

The obtained compound 15 is an example of formula III with R and $R_1$ being H, Hal is Cl, and L with Z and Z' being C=O and Y being $(CH_2)_3$, $R_3$ being OH and $X_1$ is tetraacetyl-beta-D-galactoside.

Compound 15 corresponding to structure of formula III is then reacted with compound 11 corresponding to structure II with R and $R_1$=H, $X_2$=Boc and Hal=Cl, firstly by deprotecting 11 with $BF_3OEt_2$ in $CH_2Cl_2$ and, thereafter, reacting the deprotected compound 11 with compound 15 in the presence of a base and a coupling agent, here DIPEA and PyBroP to arrive at a compound of general formula I with $X_1$ being tetra-acetyl-beta-D-galactoside, R and $R_1$ are H, Hal is Cl and L is Z and Z' being C=O and Y is $(CH_2)_3$.

In particular, the present inventors recognized that it is possible to react compound 15 with compound 11 selectively to obtain compound 16 in high yields.

In an embodiment of the present invention the protecting group of $X_1$ and $X_2$ is independently from one another selected from tert-butoxycarbonyl, benzyloxycarbonyl, tosyl, nosyl, trimethylsilyl, dimethyltertbutylsilyl, a carbohydrate unit, like, a furanose, a pyranose, a protected mono-, di- or trisaccharide including a galactoside, like beta-D-galactoside, beta-D-glucuronic acid, beta-D-glucoside, alpha-D-mannoside, fucose, a carbamate containing moiety, an acetal containing moiety, or an ether containing moiety cleavable by oxidation.

As used herein, the term "antibody" refers to naturally occurring or recombinant antibodies and also to antibody fragments. In an embodiment of the present invention, the antibodies are humanized antibodies or antibody fragments. The skilled person is well aware of suitable antibodies and antibody fragments and the production thereof. If necessary, the antibody or antibody fragments are modified allowing binding but also cleavage of the same via/at the benzolindol OH group. Furthermore, the antibody or the antibody fragments may contain of suitable linker region allowing binding but also cleavage of the same via/at the benzoindol group. Examples thereof are known in the art, e.g. WO 2017/072295 A1.

With the term "antibody compound conjugate", the conjugate of the antibody with the compound according to the present invention is meant. The compound may be a prodrug or drug. Accordingly, an embodiment of the antibody compound conjugate according to the present invention is an antibody drug conjugate (ADC).

The term "substituted" in particular with respect to alkyl, heteroalkyl, cycloalkyl, heterocycloalkyl, aryl, heteroaryl, allylsulfonyl, arylsulfonyl, alkoxy and acyl as used herein refers to said groups being substituted with one or more substituents selected from OH, =O, =S, =NR$^h$, =N—OR$^h$, S$^h$, NH$_2$, NO$_2$, NO, N$_3$, CF$_3$, CN, OCN, SCN, NCO, NCS, C(O)NH$_2$, C(O)H, C(O)OH, Halogen, R$^h$, SR$^h$, S(O)R$^h$, S(O)OR$^h$, S(O)$_2$R$^h$, S(O)$_2$OR$^h$, OS(O)R$^h$, OS(O) OR$^h$, OS(O)$_2$R$^h$, OS(O)$_2$OR$^h$, OP(O)(OR$^h$)(OR$^i$), P(O) (OR$^h$)(OR$^i$), OR$^h$, NHR$^i$, N(R$^h$)R$^i$, $^+$N(R$^h$)(R$^i$)R$^j$, Si(R$^h$)(R$^i$) R$^j$, Si(R$^h$)(R$^i$)(R$^j$), C(O)R$^h$, C(O)OR$^h$, C(O)N(R$^i$)R$^h$, OC(O) R$^h$, OC(O)OR$^h$, OC(O)N(R$^h$)R$^i$, N(R$^i$)C(O)R$^h$, N(R$^i$)C(O) OR$^h$, N(R$^i$)C(O)N(R$^i$)R$^h$ and thioderivatives of these substituents or a protonated or deprotonated form of these substituents whereby R$^h$, R$^i$, and R$^j$ are selected independently from one another from H and optionally substituted C$_{1-15}$ alkyl, C$_{1-15}$ heteroalkyl, C$_{3-15}$ cycloalkyl, C$_{3-15}$ h heterocycloalkyl, C$_{4-15}$ aryl, or C$_{4-15}$ heteroaryl or a combination thereof whereby two or more of R$^h$, R$^i$ and R$^j$ are optionally linked with each other, thus, forming a cylcoalkyl allyl or heterocyclus.

The term "alkyl" as used herein unless otherwise identified refers to straight or branched, saturated or unsaturated hydrocarbon, preferably, the alkyl group comprises from 1 to 12, such as 1 to 10 carbon atoms, i.e. 1, 2, 3, 4, 5, 6, 7, 8, 9, 10, 11 or 12 carbon atoms, preferably 1 to 8 carbon atoms, such as 1 to 6 or 1 to 4 carbon atoms. Examples of alkyl groups are methyl, ethyl, propyl, butyl, pentyl, hexyl, octyl, decyl, isopropyl, sec-butyl, isobutyl, tert-butyl, isopentyl, venyl, alyl, 1-butenyl, 2-butenly, isobutenyl, pentinyl etc.

The term "aryl" or "aromatic ring" refers to a monoradical of an aromatic cyclic hydrocarbon. Preferably, the aryl group contains 3 to 14 (e.g. 5 to 10, such as 5, 6 or 10) carbon atoms, more preferably 6 to 10 carbon atoms. These can be arranged in one ring, e.g. phenyl, or two or more condensed rings (e.g. naphthyl). Preferably aryl refers to a monocyclic ring containing 6 carbon atoms or an aromatic bicyclic ring system containing 10 carbon atoms. In some embodiments the aryl is unsubstituted in some embodiments the aryl is substituted.

The term "cycloalkyl" as used herein refers to saturated or unsaturated, non-aromatic cycloalkyl comprising 1, 2 or more rings. Examples include cyclopropyl, cyclobutyl, cyclopentyl, cyclopentenyl, cyclopentadienyl, cyclohexonyl, etc.

The term "heteroalkyl" as used herein refers to straight or branched, saturated or unsaturated hydrocarbons wherein at least one of the carbon is substituted with a heteroatom. The heteroatoms are preferably selected from S, N, O, and P.

The term "heteroaryl" refers to aromatic monoradicals composed of one or more fused aromatic ring systems. Therein at least one of the carbon atoms is substituted with a heteroatom. Suitable heteroatoms include O, N, S or P.

The term "acyl" as used herein refers to a functional group with the general formula R$_{ac}$—CH=O— wherein R$_{ac}$ refers to an optionally substituted hydrocarbon radical, in particular, a hydrocarbon chain having C$_1$-C$_8$ carbon atoms.

The term "alkylsulfonyl" or "arylsulfonyl" refer to alkyl or aryl groups containing a SO$_2$ residue.

As used herein and throughout the entire description, the term "halogen" or "halo" or "Hal" means fluoro, chluoro, bromo, or iodo.

The protecting group may have a or being a functional group. The functional group of X$_1$ may be a cleavable substrate, the cleavable substrate as used herein refers to a structure which is cleavable under appropriate conditions, namely, as identified below by way of enzymatic digestion or other physical or chemical cleavage. That is, in case that the substituent X$_1$ is a functional group in form of a substrate, cleavage of said substrate may be in the cell in specific compartments, like the lysosomes or other cellular compartments converting the prodrug into the active drug accordingly. The functional group includes carbohydrate units, like furanose and pyranose or a fucose. Further, the functional group is a disaccharide or trisaccharide. In an embodiment of the present invention, the functional group is a galactoside cleavable by galactosidase.

In an aspect of the present invention, the substituent Hal is Cl (chloro) and/or R$_1$ is H and/or wherein each R is H.

In another embodiment of the present invention, the protecting group X$_2$ is tertbutyloxycarbonyl and X$_1$ is tetraacetyl-beta-D-galactoside. In addition, in an embodiment of the present invention, the protecting group X$_2$ is tert-butyloxycarbonyl.

The protecting group X$_1$, X$_2$ and X$_4$ as defined herein may be selected independently from one another from functional groups protected mono-, di- or trisaccharids or oligosaccharids, in particular, hexose, pentose or heptose optionally representing desoxyderivates or aminoderivates therefrom. These substituents may be further substituted with substituents of halogen, C$_{1-8}$ alkyl, C$_{1-8}$ acyl, C$_{1-8}$ heteroalkyl, C$_{3-7}$ cycloalkyl, C$_{3-7}$ heterocycloalkyl, C$_{4-12}$ aryl or C$_{4-12}$ heteroaryl, amino or amido groups. Of course, other suitable substituents may be possible like labile substituents selected from semiacetal and acetal, benzyl groups and substituted benzyl groups.

In a further embodiment, the method is a method wherein the base present for reacting compound of formula II with the compound of formula III is selected from diisopropylethylamine (DIPEA), triethylamine or pyridine.

Of course other suitable bases can be used according to the present invention, the skilled person is well aware of a suitable basis accordingly.

Further, the coupling agent may be selected from known coupling agents including phosphonium agents. Suitable phosphonium agents include compounds known as PyCloP, PyBroP, PyBoP, PyAoP.

In another embodiment, the method of the present invention the moiety L has a general structure VI wherein n is an integer from 1 to 10. In an embodiment, n is an integer from 1 to 5, like 1, 2, 3, 4 and 5, in particular 3.

In another embodiment, the present invention relates to a method according to the present invention wherein the compound of formula III is obtained by reacting a compound of IV

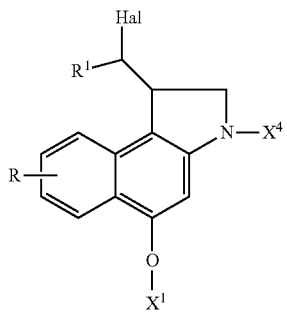

IV wherein $X_1$, R, $R_1$ and Hal are defined as above, $X_4$ is a protecting group as defined for $X_1$ and $X_1$ and $X_4$ are different from each other, with a compound of general formula VII $$R_5\text{-L-}R_6 \quad \text{VII}$$

with L having the general structure Z—Y—Z'
wherein Z, Y and Z' are defined as above and $R_5$ and $R_6$ are independently from one another selected from a halogen, like Cl; or Br, or an OH group,
whereby in a first step the compound of formula IV is deprotected at the $X_4$ group by reacting the same with a deprotecting agent and, subsequently, the deprotected compound of formula IV is reacted with the compound of formula VII in the presence of a base to obtain the compound of formula III.

As discussed with respect to scheme 1 above, the compound according to general formula IV containing the protecting group $X_4$, e.g. in form of Boc, is deprotected by known methods, e.g. by using a Lewis acid.

That is, deprotection of compounds containing a protecting group may be achieved by using a Lewis acid or a Broenstedt acid. The skilled person is well aware of suitable acids. Alternatively, the protecting group, like a carboxybenzyl group (cbz-group) may be deprotected using $H_2$ in the presence of a catalyst, like a Pd containing catalyst.

The deprotected structure IV is then allowed to react with a compound of general formula VII.

In general formula VII the definitions of Z and Z' as well as Y are as identified above, e.g. the structure Z—Y—Z' is L as defined with respect to general structure VI.

$R_5$ and $R_6$ are leaving groups, e.g. a halogen including Cl and Br or a hydroxyl group as part of a carboxyl group.

The base may be a base as defined above, like diisopropylamine (DIPEA), triethylamine or pyridine. The skilled person is well aware of suitable bases useful for this reaction.

In a further aspect, the present invention relates to a compound of formula I obtainable by a method according to the present invention.

The compounds according to the present invention are characterized in having a free hydroxyl group at one benzoindol group of the bifunctional compound of general formula I while the corresponding substituent on the second moiety of the benzoindol group is protected via a protecting group.

The compound of formula I according to the present invention encompasses compounds wherein $X_1$ itself is in a protected or unprotected form, e.g. in case of mono- or di- or trisaccharides or oligosaccharides, the saccharides are protected or unprotected. For example in case of the protecting group tetra-acetyl-beta-D-galactoside, the tetra-acetyl substituents may be absent, thus, $X_1$ is the free beta-D-galactoside accordingly.

The compounds of formula I as described above are suitable for the preparation of e.g. antibody compound conjugates wherein at least one functional group including antibodies or a binding moiety in general, are present. Binding moiety as defined herein includes the antibody or antibody fragments allowing specific binding to a binding partner. In general, a binding moiety may include any ligand allowing binding to a binding partner resulting in a binding pair including binding pairs like ligand receptor, binding to a cancer-specific epitope, and binding to a senescent cell-specific epitope.

Further, the protecting group may be a functional group in form of a substrate which may be released upon enzymatic digestion, e.g. proteolytic, oxidative or reductive cleavage by enzymes including plasmin, cathepsin, cathepsin B, beta-glucuronidase, galactosidase, mannosidase, glucosidase, neuramidase, saccharosidase, maltase, fructosidase, glycosilase, prostates specific antigen, urokinase type plasminogen activator (u-PA), metalloproteinase, cytochrome P450 or other enzymes used in enzyme product therapy like ADEPT.

In a further aspect, the present invention relates to a method for preparing an antibody drug conjugate composed of an antibody moiety and a compound according to formula I in particular as defined herein, comprising the step of coupling the antibody moiety to the compound according to formula I via the free OH group at position 5 of the benzoindol group of formula I.

The method includes the use of the compound of formula I as a starting material wherein at one of the two moieties a free OH group is present at position 5 of the benzoindol group of formula I while the other OH group at position 5 of the second benzoindol group of the second moiety is protected with a protecting group e.g. a functional group, while said protecting group itself may be protected or unprotected.

In addition, the present invention relates to the antibody compound conjugate obtainable by the method according to the present invention. In one aspect, this antibody compound conjugate is an antibody drug conjugate (ADC).

In a further aspect, the present invention relates to a method for preparing an ADC composed of two identical or two different antibody moieties and a compound according to formula I wherein $X_1$ is either absent or present comprising the step of providing an antibody compound conjugate according to the present invention, optionally deprotecting the $X_1$ group with a deprotecting agent as described herein and coupling a second antibody moiety to the antibody drug conjugate according to the present invention via the deprotected OH group at position 5 of the benzoindol group of formula I or if $X_1$ is present via the deprotected $X_1$ protecting group. For example in case of $X_1$ being a galactoside, the second antibody moiety is bound via the deprotected galactoside.

In one aspect, the antibody compound conjugate according to the present invention obtainable by the method according to the present invention contain two different antibody moieties.

In a further aspect, the present invention relates to a pharmaceutical composition containing the compound containing at least one of the compounds according to the present invention.

In some embodiments, the pharmaceutical composition for use as disclosed herein, further comprises at least one pharmaceutically acceptable carrier. In some embodiments, the compounds according to the present invention or a pharmaceutically acceptable salt, solvate or hydrate thereof may be included in a pharmaceutically acceptable carrier.

As used herein and throughout the entire description, the terms "carrier" and "excipient" are used interchangeably herein. Pharmaceutically acceptable carriers or excipients include diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), anti-foaming agents (e.g. Simethicone), thickening agents (e.g. methylcellulose or hydroxyethylcellulose), sweetening agents (e.g. sorbitol, saccharin, aspartame, acesulfame), flavoring agents (e.g. peppermint, lemon oils, butterscotch, etc), humectants (e.g. propylene, glycol, glycerol, sorbitol). The person skilled in the art will readily be able to choose suitable pharmaceutically acceptable carriers or excipients, depending, e.g., on the formulation and administration route of the pharmaceutical composition.

A non-exhaustive list of exemplary pharmaceutically acceptable carriers or excipients includes (biodegradable) liposomes; microspheres made of the biodegradable polymer poly(D,L)-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable excipients are inter alia described in Remington's Pharmaceutical Sciences, $15^{th}$ Ed., Mack Publishing Co., New Jersey (1991) and Bauer et al., Pharmazeutische Technologie, $5^{th}$ Ed., Govi-Verlag Frankfurt (1997).

The pharmaceutical composition of the invention will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed in accordance with the invention for delivery by any suitable route of administration. In the context of the present invention, the routes of administration include:

topical routes (such as epicutaneous, inhalational, nasal, opthalmic, auricular/aural, vaginal, mucosal) and aerosols;

enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

In some embodiments the administration may be a parenteral route, in particular intravenous or intramuscular.

In some embodiments, the pharmaceutical composition, as disclosed herein, is administered to a subject in need thereof in an amount effective to treat cancer. The subject is preferably a mammal.

As used herein and throughout the entire description, the term "Subject" means eukaryotes, like animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. The subject is preferably a mammal, more preferably a human.

As used herein and throughout the entire description, the term "amount effective" in the context of a composition or dosage form for administration to a subject refers to an amount of the composition or dosage form sufficient to provide a benefit in the treatment of cancer, to delay or minimize symptoms associated with cancer, or to cure or ameliorate cancer. In particular, a therapeutically effective amount means an amount sufficient to provide a therapeutic benefit in viva Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In a further aspect, the present invention relates to the use of the compound according to the present invention for the treatment of senescence associated disorders or disease.

As used herein, senescence-associated disorders or diseases include disorders or diseases associated with, or caused by cellular senescence, including age-related diseases and disorders. A senescence-associated disease or disorder may also be called a senescent cell-associated disease or disorder. A prominent feature of aging is a gradual loss of function, or degeneration that occurs at the molecular, cellular, tissue, and organismal levels. Age-related degeneration gives rise to well-recognized pathologies such as sarcopenia, atherosclerosis and heart failure, osteoporosis, pulmonary insufficiency, renal failure, neurodegeneration (including macular degeneration, Alzheimer's disease, and Parkinson's disease), and many others.

Senescence-associated diseases and disorders include, but are not limited to, cardiovascular diseases and disorders, inflammatory diseases and disorders, autoimmune diseases and disorders, pulmonary diseases and disorders, eye diseases and disorders, metabolic diseases and disorders, neurological diseases and disorders (e.g., neurodegenerative disease and disorders); age-related diseases and disorders induced by senescence; skin conditions; age-related diseases; dermatological diseases and disorders; and transplant related diseases and disorders.

Preferably, the subject is a mammal, preferably a human.

In one preferred embodiment of the invention, the senescence associated disease or disorder is a proliferative disorder, such as cancer or leukemia including lymphoma. In another preferred embodiment, the senescence associated disease or disorder is a cardiovascular disease. A further embodiment of the invention of the senescence associated disease or disorder is an inflammatory or autoimmune disease or disorder.

Another embodiment relates to neurological disease or disorders as senescence associated disease or disorder. Further senescence associated disease or disorder include ophthalmic diseases and disorders as well as metabolic disease and pulmonary disease or disorder.

Further senescence associated diseases or disorders refer to age-related disorders as well as dermatological diseases or disorders and lifespan and age-related diseases or conditions. Moreover, the present application, namely, the use of the compound according to the present invention wherein $X_1$ is e.g. a galactoside refers to diseases or disorders which correlates or associated with elevated β-galactosidase activity.

Moreover, the present invention relates to the use of the compound according to the present invention for treatment of tumors, in particular, in mammals, the use is particularly possible in ADEPT therapy.

Furthermore, the present invention relates to the use of the compound according to formula I for the preparation of an antibody drug conjugate.

The present invention will be described further by way of examples without limiting the same thereto.

EXAMPLES

Experimental Procedures
General Methods

Unless stated otherwise, experiments were conducted under air. Reagents were obtained from commercial sources and used without purification. Anhydrous $CH_2Cl_2$ (Analytical grade, Fischer Scientific) and THF (AnaIR NORMA-PUR, VWR) were obtained by the addition of vacuum oven (Vacutherm 6025 from Heraeus Instruments) dried 3 Å molecular sieves to an argon-flushed bottle. DMF (peptide synthesis grade, Fischer Scientific) was used throughout. NMR spectra were recorded on Mercury-300, Unity-300, Inova-500 and Inova-600 spectrometers from Varian and on an AMX-300 spectrometer from Bruker. Chemical shifts are reported in parts per million (ppm) from high to low frequency using the residual solvent peak as the internal reference (DMSO=2.50 ppm).

All $^1H$ resonances are reported to the nearest 0.01 ppm. The multiplicity of $^1H$ signals are indicated as: s=singlet; d=doublet; t=triplet; q=quartet; sept=septet; m=multiplet; br=broad; app=apparent; or combinations of thereof. Coupling constants (J) are quoted in Hz and reported to the nearest 0.1 Hz. Where appropriate, averages of the signals from peaks displaying multiplicity were used to calculate the value of the coupling constant. $^{13}C$ NMR spectra were recorded on the same spectrometer with the central resonance of the solvent peak as the internal reference (DMSO=39.52 ppm) $^{13}C$ resonances are reported to the nearest 0.01 ppm. DEPT, COSY, HSQC and HMBC experiments were used to aid structural determination and spectral assignment. Fully characterized compounds were chromatographically homogeneous. Flash column chromatography was carried out on an automated system (Isolera One from Biotage) using Biotage SNAP Flash Cartridges KP-Sil (Silica 55 Å, 53 µm, 96.95% between 30-90 µm) or Interchim PF-15SIHP (High Performance Spherical Silica, 15 µm) as the stationary phase. Preparative TLC was performed using Silica Gel GF UV254 20×20 cm 2000 micron plates (Analtech) or RP-18W/$UV_{254}$ 5×20 cm 250 micron plates (Macherey-Nagel) and smaller quantities (<10 mg of crude material) were purified on analytical TLC Silica gel 60 $F_{254}$ plates (Merck, Germany). TLC was visualized using both short and long waved ultraviolet light in combination with standard laboratory stains (acidic potassium permanganate, acidic ammonium molybdate and ninhydrin). ESI-MS and ESI-HRMS spectra were recorded on an Apex IV spectrometer from Bruker Daltronik. EI-MS and EI-HRMS spectra were recorded on a MAT 95 spectrometer from Finnigan. Melting points (Mp) were determined using an EZ-Melt Automated Melting Point Apparatus from Standford Research Systems and are not corrected. IR spectra were recorded on an FT/IR-4100 spectrometer from Jasco. All substances were applied neat on an ATR unit. UV spectra were recorded on a V-630 spectrometer from Jasco. Optical rotations were measured on a JASCO P-2000 polarimeter. Measurements were conducted using a sodium lamp (λ 589 nm, D-line); $[\alpha]_D^{20}$ values were reported in 10 deg $cm^2$ $g^{-1}$, concentration (c) in g per 100 ml. Preparative HPLC was performed with a Kromasil 100 C18 (7.5 µm particle size, 250×200 mm, Dr. Maisch GmbH) column on a Jasco HPLC system with binary pump and UV-detector. Analytical HPLC was performed with a Kromasil 100 C18 (5.0 µm particle size, 250×4 mm, Dr. Maisch GmbH) or a Chiralpak IA (5 µm Particle size, 250×4.6 mm, Daicel Corporation) column on a Jasco HPLC system with UV- and DAD-detector.

Unless stated otherwise, hydrogenations were carried out at rt on a ThalesNano Nanotechnology H-Cube system (Pd/C 10 wt. % loading cell) in full hydrogen mode with a flow rate of 1.0 mL/min.

tert-butyl (S)-1-(chloromethyl)-5-hydroxy-1,2-dihydro-3H-benzo[e]indole-3-carboxylate (11)

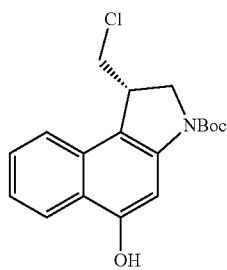 [SMILES: CC(C)(C)OC(=O)N1C[C@@H](CCl)c2c1cc(O)c1ccccc21]

To an argon filled flask containing the benzyl ether of CBI 11 (200 mg, 0.472 mmol) and Pd/C (10 wt. % loading, 100 mg, 0.940 mmol) was added dry THF (20 mL). The argon was carefully replaced by hydrogen with a balloon and the reaction mixture was heated to 40° C. for 10 h. The mixture was filtered over celite and the residue washed with EtOAc (3×50 mL). The combined filtrate was concentrated under reduced pressure and purified by flash column chromatography (CH$_2$Cl$_2$/EtOAc, 94:6) to afford the title compound (113 mg, 0.340 mmol) as a white solid in 72% yield.

R$_f$ 0.45 (CH$_2$Cl$_2$/EtOAc, 92:8) 0.39 for dechlorinated product (2R,3S,4S,5R,6S)-2-(Acetoxymethyl)-6-(((S)-3-(tert-butoxycarbonyl)-1-(chloro-methyl)-2,3-dihydro-1H-benzo[e]indol-5- yl)oxy)tetrahydro-2H-pyran- 3,4,5-triyl triacetate (13)

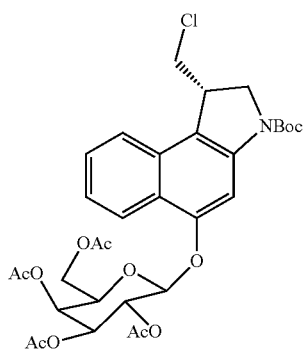 [SMILES: CC(=O)OCC1OC(Oc2cc3c(c4ccccc24)[C@H](CCl)CN3C(=O)OC(C)(C)C)C(OC(C)=O)C(OC(C)=O)C1OC(C)=O]

To a flask charged with naphthol 11 (138 mg, 0.413 mmol), tetraacetyl-β-D-galactosyl-trichloracetimidat 12 (265 mg, 0.537 mmol) and 3 Å molecular sieves was added dry CH$_2$Cl$_2$ (21 mL) under an argon atmosphere. The mixture was stirred for 30 min and a solution of boron trifluoride diethyl etherate (26 µL, 0.21 mmol) in dry CH$_2$Cl$_2$ (2.0 mL) was added at −10° C. The reaction mixture was stirred for 3 h at −10° C. and concentrated under reduced pressure. Purification by flash column chromatography (PET/EtOAc, 1:0 to 1:1) furnished the desired compound (223 mg, 0.336 mmol) as a white solid in 81% yield.

5-((S)-1-(chloromethyl)-5-(((2S,3R,4S,5S,6R)-3,4,5-triacetoxy-6-(acetoxymethyl)tetrahydro-2H-pyran-2-yl)oxy)-1,2- dihydro-3H-benzo[e]indol-3-yl)-5-oxopentanoic acid (15)

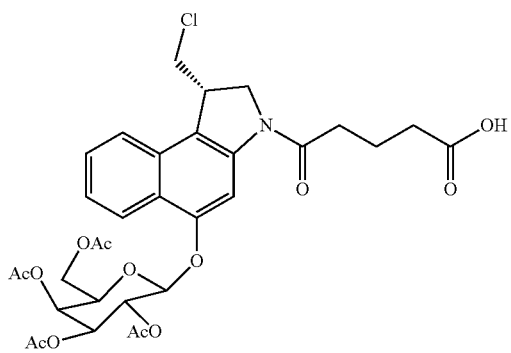 [SMILES: CC(=O)OCC1OC(Oc2cc3c(c4ccccc24)[C@H](CCl)CN3C(=O)CCCC(=O)O)C(OC(C)=O)C(OC(C)=O)C1OC(C)=O]

The CBI tetraacetyl-β-D-galactoside 13 (50 mg, 0.075 mmol) was taken up in CH$_2$Cl$_2$ (3.0 mL) and two drops of boron trifluoride diethyl etherate were added at 0° C. The reaction mixture was allowed to warm to rt and stirred for another 2 h. Upon completion, the mixture was concentrated under reduced pressure and dissolved in peptide grade DMF (1 mL). The resulting solution was cooled to 0° C. and slowly added to a freshly prepared solution of glutaryl dichloride 14 (0.19 g, 1.1 mmol) in peptide grade DMF (1 mL) at 0° C. After dropwise addition of DIPEA (0.20 mL), the reaction mixture was stirred for 30 min and concentrated under reduced pressure. Flash column chromatography (CH$_2$Cl$_2$/MeOH, 100:0 to 96:4) yielded the title compound (41 mg, 0.061 mmol) as a pale brown solid in 80% yield.

R$_f$ 0.74 (EtOAc)

Mp 155° C.

$^1$H-NMR (500 MHz, DMSO-d$_6$): δ 8.29 (s, 1H), 7.91 (d, J=8.4 Hz, 1H), 7.88 (d, J=8.4 Hz, 1H), 7.56 (app t, J=7.2 Hz, 1H), 7.41 (app t, J=7.4 Hz, 1H), 5.57 (d, J=6.5 Hz, 1H), 5.45-5.38 (m, 3H), 4.55 (dd, J=7.5, 4.5 Hz, 1H), 4.34 (app t, J=9.8 Hz, 1H), 4.26-4.14 (m, 3H), 4.07 (dd, J=11.5, 7.8 Hz, 1H), 4.01 (dd, J=10.9, 3.0 Hz, 1H), 3.88 (dd, J=11.0, 7.4 Hz, 1H), 2.66-2.46 (m, 2H), 2.34 (app t, J=7.4 Hz, 2H), 1.83 (m, 2H)

$^{13}$C-NMR (126 MHz, DMSO-d$_6$): δ 174.39, 170.69, 170.38, 170.12, 169.76, 169.56, 153.04, 141.77, 129.61, 127.74, 124.11, 122.99, 122.03, 121.97, 117.92, 101.43, 98.83, 70.92, 69.83, 68.53, 67.54, 61.84, 52.62, 47.73, 40.66, 34.24, 32.97, 20.59, 20.47, 20.43, 20.43, 19.57

HRMS (ESI) m/z calc for C$_{32}$H$_{35}$ClNO$_{13}$ [M−H]$^−$: 676.1797, found 676.1797.

(2R,3S,4S,5R,6S)-2-(acetoxymethyl)-6-(((S)-1-(chloromethyl)-3-(5-(((S)-1-(chloromethyl)-5-hydroxy-1,2-dihydro-3H-benzo[e]indol-3-yl)-5-oxopentanoyl)-2,3-dihydro-1H-benzo[e]indol-5-yl)oxy) tetrahydro-2H-pyran-3,4,5-triyl triacetate (16)

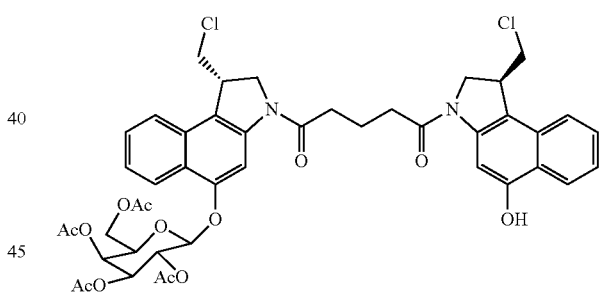

The CBI-tetraacetyl-β-D-galactoside-pentadioate monoamide 15 (12 mg, 0.035 mmol) was taken up in CH$_2$Cl$_2$ (2 mL) and 3 drops of boron trifluoride diethyl etherate were added at 0° C. The reaction mixture was allowed to warm to rt and the deprotection was monitored by TLC. After 2 h the reaction mixture was concentrated under reduced pressure and the crude solid was kept under high-vacuum for 1 additional hour. Acid 5 (20 mg, 0.030 mmol), molecular sieves (3 Å) and DMF (0.30 mL) were added to the solution under an argon atmosphere. The resulting mixture was cooled to −20° C. and PyBroP (16 mg, 0.035 mmol) and DIPEA (15 µL, 0.089 mmol) were added sequentially. The reaction mixture was kept at −20° C. overnight and allowed to warm up to 0° C. the next day. The reaction was stirred for another 8 h at that temperature and subsequently concentrated under reduced pressure The crude product was purified by flash column chromatography (PET/EtOAc, 1:0 to 3:7) to give 16 as a pale brown solid (14 mg, 0.016 mmol) in 44% yield.

$R_f$ 0.51 (EtOAc/PET, 2:1)

Mp 155° C.

Optical rotation $[\alpha]_D^{20}$=−41.5 (c 0.27, CHCl$_3$)

$^1$H-NMR (600 MHz, DMSO-d$_6$): δ 10.31 (s, 1H), 8.33 (br s, 1H), 8.09 (d, J=8.2 Hz, 1H), 8.02 (br s, 1H), 7.94 (d, J=8.5 Hz, 1H), 7.89 (d, J=8.4 Hz, 1H), 7.78 (d, J=8.4 Hz, 1H), 7.56 (m, 1H), 7.49 (m, 1H), 7.42 (m, 1H), 7.32 (m, 1H), 5.56 (m, 1H), 5.43-5.41 (m, 2H), 5.40 (m, 1H), 4.54 (dd, J=7.1, 4.8 Hz, 1H), 4.38 (app t, J=10.2 Hz, 1H), 4.33 (app t, J=10.0 Hz, 1H), 4.27-4.21 (m, 2H), 4.20-4.13 (m, 3H), 4.10 (dd, J=11.4, 7.7 Hz, 1H), 4.03 (dd, J=11.1, 3.1 Hz, 1H), 3.99 (dd, J=11.1, 3.0 Hz, 1H), 3.89 (dd, J=11.1, 7.4 Hz, 1H), 3.79 (dd, J=10.8, 8.3 Hz, 1H), 2.77-2.67 (m, 2H), 2.66-2.57 (m, 2H), 2.18 (s, 3H), 2.08 (br s, 3H), 2.02 (s, 3H), 2.01-1.95 (m, 2H), 1.97 (s, 3H)

$^{13}$C-NMR (126 MHz, DMSO-d$_6$): δ 170.62, 170.37, 169.94, 169.72, 169.35, 169.16, 154.03, 152.79, 141.81, 141.53, 129.77, 129.41, 127.44, 126.98, 123.82, 122.90, 122.71, 122.42, 122.30, 121.90, 121.78, 121.46, 117.75, 113.56, 101.50, 99.70, 98.78, 70.75, 69.75, 68.48, 67.38, 61.57, 52.58, 52.58 47.53, 47.53 40.74, 40.74, 34.39, 25.03, 20.48, 20.34, 20.34, 20.30, 19.15

LRMS (ESI) m/z calc for C$_{45}$H$_{46}$Cl$_2$N$_2$NaO$_{13}$ [M+Na]$^+$: 915.3, found 915.3 (100), C$_{45}$H$_{47}$Cl$_2$N$_2$O$_{13}$ [M+H]$^+$: 893.3, found 893.2 (24).

HRMS (ESI) m/z calc for C$_{45}$H$_{46}$Cl$_2$N$_2$NaO$_{13}$ [M+Na]$^+$: 915.2269, found 915.2263.

The invention claimed is:

1. A method for the synthesis of a compound of general formula I

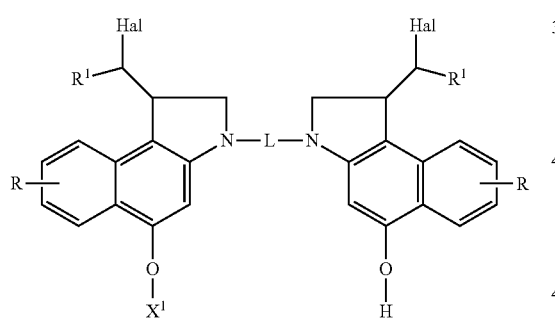

wherein Hal is F, Cl, Br, or I;

R is H or an optionally substituted C$_1$-C$_4$ alkyl group, an optionally substituted C$_1$-C$_4$ alkoxy group, an optionally substituted aryl group, an optionally substituted heteroaryl group, an optionally substituted C$_1$-C$_4$ alkyl carboxy C$_1$-C$_4$ alkyl group, Hal, CN, an optionally substituted C$_1$-C$_4$ alkylsulfonyl group, an optionally substituted arylsulfonyl group, or an NR$_z$ group as defined below;

R$_1$ is H or a C$_1$-C$_4$ alkyl group or a C$_1$-C$_4$ alkoxy group;

X$_1$ is a protecting group;

L is a connecting group for covalent linkage whereby L has the general structure Z—Y—Z';

Z and Z' are independently from one another selected from C=O, OC=O, SO$_2$, NRz, NR$_2$C=O, C=ONR$_z$, wherein each R$_z$ is independently from one another selected from H, optionally substituted C$_1$-C$_4$ alkyl group or optionally substituted C$_1$-C$_4$ acyl;

wherein Y is an optionally substituted C$_1$-C$_{10}$ alkyl group, or a group of structure VIII

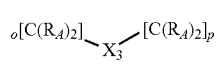

wherein o and p are independently from one another selected from an integer of 1 to 20, whereby o and p may be the same integer or a different integer, X$_3$ is i) N, S or O, or ii) an aryl group or a heteroarylgroup, wherein [C(R$_a$)$_2$]$_o$ and [C(R$_a$)$_2$]$_p$ are present in the metaposition of said aryl group or said heteroaryl group, each R$_A$ is independently from one another selected from H or an optionally substituted C$_1$-C$_4$ alkyl group or an optionally substituted C$_1$-C$_4$ acyl group; comprising:

reacting a compound of formula II

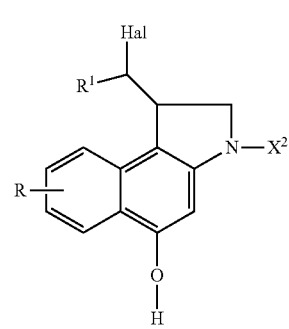

wherein R, R$_1$, and Hal are defined as above and X$_2$ is a protecting group which may be identical or different to X$_1$ above, with a deprotecting agent for deprotecting the X$_2$ group from the compound of formula II; and subsequently, reacting the deprotected compound of formula II with a compound of formula III

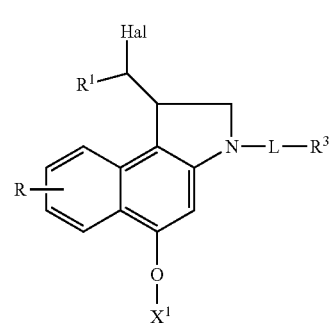

wherein the substituents Hal, R$_1$, X$_1$ and R are defined as above and L is a connecting group as defined above, R$_3$ is selected from Hal, and OH in the presence of a coupling agent and a base to obtain a compound of formula I.

2. The method of claim 1 wherein the protecting group of X$_1$ and X$_2$ is independently from one another selected from the group consisting of a functional group selected from the group consisting of tert-butoxycarbonyl, benzyloxycarbonyl, tosyl, nosyl, trimethylsilyl, and dimethyltertbutylsilyl, a protected mono-, di- or trisaccharide selected from the group consisting of beta-D-galactoside, beta-D-glucuronic acid, beta-D-glucoside, and alpha-D-mannoside, fucose, a carbamate containing moiety, an acetal containing moiety, and an ether containing moiety cleavable by oxidation.

3. The method according to claim 1 wherein

Hal is Cl, and/or $R_1$ is H, and/or

R is H.

4. The method according to claim 1 wherein $X_2$ is tert-butyloxycarbonyl and $X_1$ is tetraacetyl-beta-D-galactoside.

5. The method according to claim 1 wherein the base is selected from the group consisting of diisopropylethylamine, triethylamine, and pyridine.

6. The method according to claim 1 wherein the coupling agent is a phosphonium agent.

7. The method according to claim 1 wherein L has the general structure VI

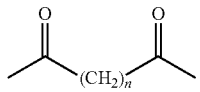

VI wherein n is an integer from 1 to 10.

8. The method of claim 1 wherein the step of reacting the deprotected compound of formula II with a compound of formula III is preceded by a step of forming the compound of formula III by reacting a compound of formula IV

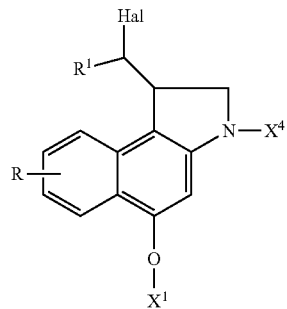

IV wherein $X_1$ and $X_4$ are each protecting groups and are different from each other, and R, $R_1$ and Hal are defined as above, with a compound of general formula VII $R_5$-L-$R_6$　　　VII with L being Z—Y—Z' and wherein Z, Y and Z' are defined as above and $R_5$ and $R_6$ are independently from one another selected from a halogen or an OH group, whereby in a first step the compound of formula IV is deprotected at the $X_4$ group by reacting the same with a deprotecting agent and, subsequently, the deprotected compound of formula IV is reacted with the compound of formula VII in the presence of a base to obtain the compound of formula III.

* * * * *